United States Patent
Banerjee et al.

(10) Patent No.: US 6,485,709 B2
(45) Date of Patent: Nov. 26, 2002

(54) DENTAL BLEACHING GEL COMPOSITION, ACTIVATOR SYSTEM AND METHOD FOR ACTIVATING A DENTAL BLEACHING GEL

(75) Inventors: Abhijit Banerjee, Plainsboro, NJ (US); Joshua Friedman, Ridgefield, CT (US)

(73) Assignee: AdDent Inc., Danbury, CT (US)

( * ) Notice: Subject to any disclaimer, the term of this patent is extended or adjusted under 35 U.S.C. 154(b) by 0 days.

(21) Appl. No.: 09/767,384

(22) Filed: Jan. 23, 2001

(65) Prior Publication Data

US 2002/0141949 A1 Oct. 3, 2002

(51) Int. Cl.[7] .............................. A61K 7/20; A61K 7/28
(52) U.S. Cl. ...................... 424/53; 424/50; 433/215; 433/216; 433/217.1; 8/111
(58) Field of Search .................. 424/53, 50; 433/215, 433/216, 217.1; 15/167.1

(56) References Cited

U.S. PATENT DOCUMENTS

| | | | | |
|---|---|---|---|---|
| 4,564,519 A | * | 1/1986 | Pollico et al. ................. | 424/50 |
| 4,728,455 A | * | 3/1988 | Rerok .......................... | 252/99 |
| 4,842,846 A | * | 6/1989 | Nakano ........................ | 424/50 |
| 4,980,154 A | * | 12/1990 | Gordon ........................ | 424/53 |
| 5,032,178 A | * | 7/1991 | Cornell ........................ | 106/35 |
| 5,055,287 A | * | 10/1991 | Kessler ........................ | 424/53 |
| 5,071,439 A | * | 12/1991 | Welbel ......................... | 8/111 |
| 5,194,416 A | * | 3/1993 | Jurollor et al. .............. | 502/167 |
| 5,262,151 A | * | 11/1993 | Montgomery ................ | 424/50 |
| 5,264,001 A | * | 11/1993 | Arifiglu et al. ................ | 8/111 |
| 5,356,554 A | * | 10/1994 | Delwel et al. ................ | 252/94 |
| 5,403,578 A | * | 4/1995 | Gordon ........................ | 424/53 |
| 5,536,441 A | * | 7/1996 | Chapple et al. ......... | 252/186.33 |
| 5,554,197 A | * | 9/1996 | Assini et al. .................. | 8/406 |
| 5,611,687 A | * | 3/1997 | Wagner ........................ | 433/80 |
| 5,648,064 A | * | 7/1997 | Gaffar et al. ................. | 424/53 |
| 6,030,222 A | * | 2/2000 | Tarver ...................... | 433/217.1 |
| 6,108,850 A | * | 8/2000 | McLaughlin ............... | 15/167.1 |
| 6,149,895 A | * | 11/2000 | Kutch .......................... | 424/53 |
| 6,155,832 A | * | 12/2000 | Wiesel ....................... | 433/215 |
| 6,036,493 A1 | | 3/2002 | Sharma ...................... | 433/216 |

* cited by examiner

Primary Examiner—Shep K. Rose

(57) ABSTRACT

A dental bleaching gel composition having a long shelf life for use with an activator system to cause accelerated bleaching action of a peroxide bleaching agent in the bleaching gel composition when applied upon a tooth surface and to a method for applying and activating a dental bleaching gel upon a tooth surface for cosmetically whitening the tooth and/or for the treatment of stains or discolorations over a shortened time period. The dental bleaching gel has a pH independent thickening agent, a stabilizing agent for the peroxide bleaching agent and a FD & C approved dye. The activator system comprises an activator for accelerating the bleaching action of the peroxide bleaching agent and an applicator for storing the activator in a dry form separated from the bleaching gel composition such that upon contacting the applicator to the bleaching gel composition the peroxide bleaching agent contained in the gel is activated with the applicator being used to substantially simultaneously apply the bleaching gel to the tooth or teeth to be bleached.

18 Claims, 1 Drawing Sheet

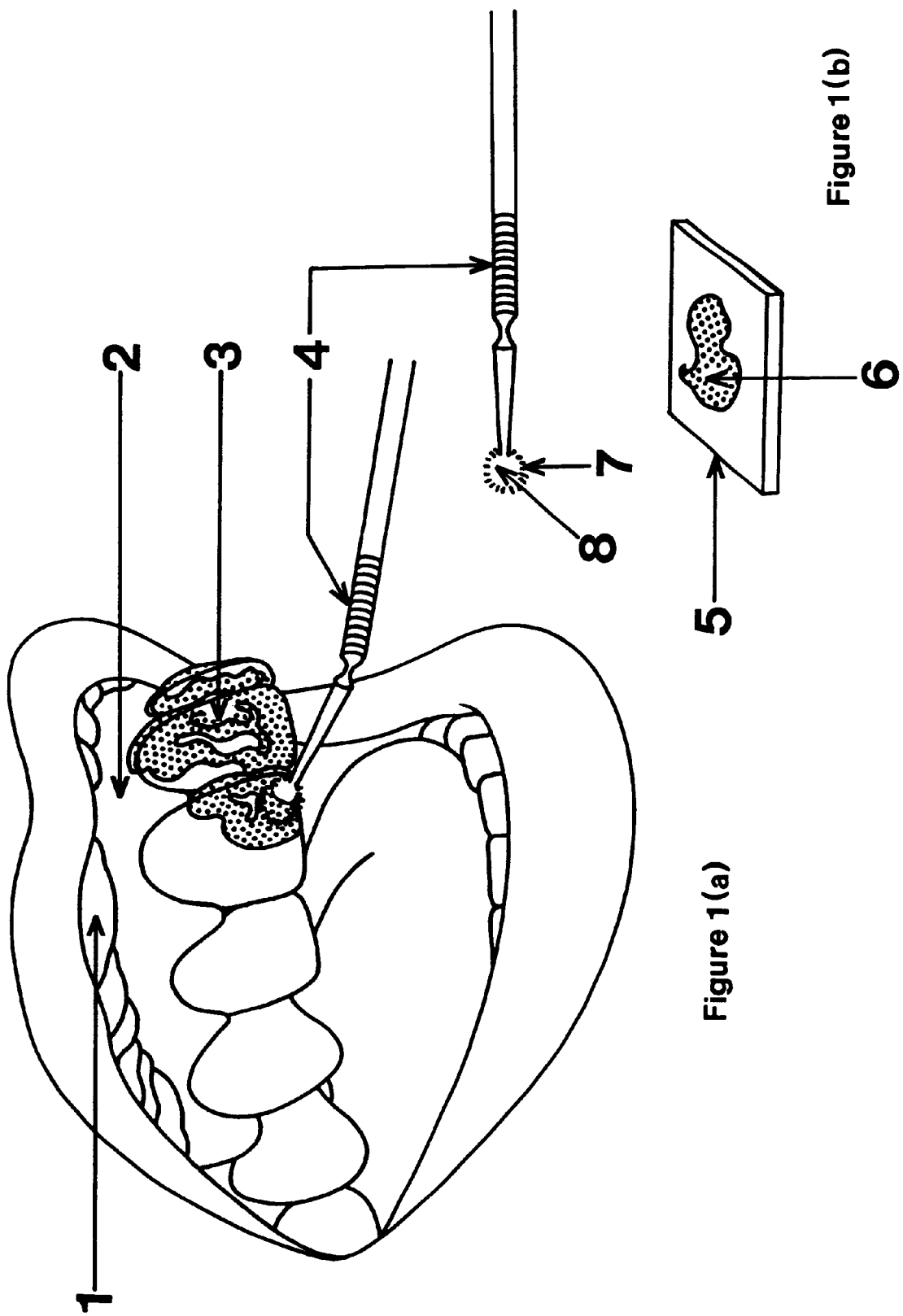

DENTAL BLEACHING GEL COMPOSITION, ACTIVATOR SYSTEM AND METHOD FOR ACTIVATING A DENTAL BLEACHING GEL

BACKGROUND OF THE INVENTION

1. The Field of the Invention

The present invention is directed to a dental bleaching gel composition having a long shelf life for use with an activator system and to an activator system for a bleaching gel to cause accelerated bleaching action upon a tooth surface over a relatively short time period and to a method for applying and activating a dental bleaching gel upon a tooth surface for cosmetically whitening the tooth and/or for the treatment of stains or discoloration over a shortened time period.

2. Relevant Technology

Conventional bleaching formulas containing a peroxide-bleaching agent such as hydrogen peroxide run the risk of poor shelf life unless the formulation includes a stabilizer for the bleaching agent. The stabilizer functions to inhibit the breakdown of the peroxide bleaching agent by slowing down the dissociation of the peroxide thereby prolonging its potency over a longer time period. Although shelf life is extended by slowing down the bleaching action the effectiveness of the bleaching composition to whiten teeth is substantially reduced. This, in turn, necessitates repeated applications to achieve a cumulative effect and may require as many as ten applications or more to visually notice any change particularly with low concentration peroxide formulations. Professional treatment on the other hand, generally performed in the dental office, utilizes a high concentration of peroxide bleaching agent of up to 35 wt % of the formulation. Although this is more effective than that of lower peroxide formulations the higher concentration of peroxide requires a proportionally higher concentration of stabilizer to satisfy the shelf life requirements of the regulatory authorities in different countries and, as such, still relies on numerous repeated office visits of from 2 to 6 visits to ultimately cause a sufficient clinically effective cumulative effect satisfactory to the patient. In the United States a peroxide bleaching agent formulation must have a shelf life of at least six months at room temperature. Accordingly, all conventional in-office-bleaching formulations presently depend upon lengthy repeated office visits of over two and more generally over four or more visits to produce whitening satisfactory to a patient. The need for so many applications and/or visits is most undesirable to the patient and uneconomical to a professional practitioner, and as such, most dentists prefer to utilize home bleaching methods.

In-office bleaching compositions are presently categorized as being either a "one-part" or "two-part" system. The distinction is based upon whether all of the components of the bleaching composition are self-contained in a desired pre-mixed proportion or if the active ingredients are isolated and need to be mixed and proportioned before use. In the "two-part" system the components which would otherwise interact with the peroxide bleaching agent are physically separated from one another. The "one-part" system making is much more attractive based upon convenience of application and in sharp contrast to the "two-part" system which is associated with the prior art requirement of both mixing and proportioning the isolated components prior to use. In fact a "two-part" system which relies upon using an aqueous solution for the bleaching composition is also subject to dangerous splattering. Another serious problem with the two part systems of prior art is that the concentration of the peroxide is reduced by 50% when a 1:1 ratio is mixed together. However, in reality, the distinction between a "one-part" and "two-part" system has no significance clinically or upon the end result. Accordingly, what should be of concern is the ability to independently control the activity of the peroxide bleaching agent to minimize the need for repeated applications and or office visits while at the same time achieving extended shelf life.

The present invention is directed to a bleaching composition in the form of a gel for use with an activator system which combines the features of both the "one-part" system and the "two-part" system for providing enhanced and independent control over the rate of activity of the peroxide bleaching agent to whiten teeth without affecting shelf life. Moreover the bleaching composition of the present invention permits an FD & C ("Federal Drug and Cosmetic") approved dye to be combined together with a peroxide bleaching agent in the bleaching composition so that a visual indication of the bleaching material in contrast to the tooth and gingiva is possible thereby providing greater control over the bleaching procedure. The bleaching action and rate of activity of the peroxide bleaching agent is controlled by the activator system which is simultaneously applied to the tooth or teeth to be bleached. Commercially available bleaching gels cannot tolerate an FD & C approved dye together with the bleaching agent particularly at higher concentrations of bleaching agent because the dye would be bleached. The peroxide bleaching agent should preferably be in a concentration of at least about 15 wt %.

The bleaching composition of the present invention is a gel formulation, which is used in conjunction with an activator system which gives the user and professional practitioner the look, feel and handling characteristics of a "one part" system in that no mixing and proportioning of any ingredients is involved. The bleaching gel of the present invention provides significant control over the bleaching operation both in terms of the rate of bleaching and the visual color indication due to the presence of an FD & C approved dye together with the bleaching agent and most important provides significant reduction in the number of office visits necessary because of the high rate of bleaching action. The bleaching action is controlled by the activator system, which accelerates the dissociation of the peroxide bleaching agent into hydroxyl and perhydroxyl free radicals to provide quick and highly efficient whitening of the tooth or teeth surfaces under treatment. Moreover, in accordance with the present invention since the activation of the peroxide bleaching agent occurs essentially simultaneously with the direct application of the bleaching gel to the tooth or teeth surfaces to be bleached a simulated "one-part" system is achieved with the convenience of use of the "one-part" system and the attributes of the "two-part" system.

SUMMARY OF THE INVENTION

The present invention relates to a dental bleaching composition comprising of a peroxide bleaching agent, a thickening agent to form a viscous gel, at least one FD & C approved dye and at least one bleaching agent stabilizer with the bleaching composition having a pH of less than 7 for use with an activator system including an activator selected from the group consisting of Manganous Chloride, Manganous Citrate, Ferrous Sulfate, Sodium Carbonate or Bicarbonate and Catalase.

The present invention also relates to an activator system for activating a bleaching composition in the form of a gel containing a stabilized peroxide bleaching agent in which the activator system comprises an activator for accelerating the bleaching action of the peroxide bleaching agent and an applicator for storing the activator in a dry form separated from the bleaching composition such that upon contacting the applicator to the bleaching composition the peroxide bleaching agent is activated. The activator preferably consists of particles of a dried compound selected from either a catalyst, an enzyme or a pH modifier to increase the pH to above at least 7. The most preferred activator is a compound selected from the group consisting of Manganous Chloride, Manganous Citrate, Ferrous Sulfate, Sodium Carbonate, Sodium Bicarbonate and Catalase.

The present invention further relates to a method for applying and activating a dental bleaching gel upon a tooth surface for cosmetically whitening the tooth and/or for the treatment of stains or discolorations comprising the steps of:

formulating a stabilized dental bleaching composition comprising a peroxide bleaching agent, a thickening agent to form a viscous gel, at least one FD & C approved dye and at least one stabilizer for said peroxide bleaching agent with the bleaching composition having a pH of less than 7;

forming an activator system to accelerate the bleaching action of the bleaching composition with the activator system comprised of an applicator and an activator of dried particles stored in the applicator with the particles selected from the group consisting of a catalyst, an enzyme or a pH modifier adapted to increase the pH of the bleaching composition upon contact to a pH of above at least 7;

contacting the applicator containing the stored dried particles of activator to the stabilized dental bleaching composition; and applying the applicator substantially immediately following contact with the bleaching composition to the tooth or teeth surfaces to be bleached.

BRIEF DESCRIPTION OF THE DRAWINGS:

The advantages of the present invention will become apparent from the following detailed description of the invention, which should be read in conjunction with the accompanying drawings of which:

FIG. 1($a$) is a view in perspective showing the bleaching gel of the present invention deposited on a pad and an activator system for activating the bleaching gel and for applying the activated bleaching gel to a tooth or teeth to be bleached; and FIG. 1($b$) is an illustrative view of human dentition in the process of being bleached using the bleaching gel and activator system of FIG. 1($a$).

DETAILED DESCRIPTION OF THE PREFERRED EMBODIMENTS OF THE INVENTION

The bleaching gel 6 shown deposited on the pad 5 of FIG. 1($a$) comprises a bleaching composition containing a per-oxide bleaching agent in a concentration of preferably above 15 wt % of the bleaching composition, a viscosity thickening agent to form a smooth viscous gel, at least one FD & C approved dye and at least one stabilizer for the bleaching agent with the components selected such that the bleaching composition will possess a pH of less than 7. The bleaching composition of the present invention has a six-month shelf life at room temperature and a shelf life at 4° C. in a regular refrigerator for at least 12 months. The dental bleaching agent maintains at least 80% of its original strength for about 12 months after manufacture of the bleaching composition and at least 95% of its original strength for about 6 months after manufacture of the bleaching composition. The various components of the bleaching gel of the present invention will hereafter be discussed separately.

Bleaching Agent

Any commercially available peroxide-containing compound may be used as the peroxide bleaching agent in the bleaching composition of the present invention. The peroxide containing compound may be selected from peroxides such as hydrogen peroxide or a complex thereof such as percabonates, and perborates of the alkaline and alkaline-earth metals. A commonly used bleaching agent is carbamide or urea peroxide ($(CONH_2)_2$—$H_2O_2$). There are a number of suitable commercially available products which employ carbamide peroxide such as "Gly-Oxide" a trademark product of Marion Labs, "Proxigel" a trademark product of Reed & Carnick, "Opalescense" a trademark product of Ultradent, etc. Other bleaching agents which are suitable employ peroxyacetic acid ($CH_3C$=$OO$—$OH$) and sodium perborate. The bleaching agent is generally selected based upon the desired concentration of the peroxide bleaching agent in the bleaching formulation. Concentrations of the peroxide agent above 15 wt % and in a range of 15 wt % to 36 wt % are preferred. The preferred peroxide bleaching agent for the bleaching composition of the present invention is "Peral-kali" which is a trade name of a commercially available stabilized grade of $H_2O_2$ solution (available in a range of from about 10–35% by wt.) through Degussa Chemicals.

Thickening Agent

The thickening or gelling agent imparts high viscosity to the formulation so that it can stay on the surface of the stained teeth in a vertical configuration for a long enough duration to impart bleaching action. The thickening agent should be inert and should not be prone to oxidation by $H_2O_2$. The gelling action preferably should occur independent of pH so that the stability of $H_2O_2$ would not be compromised even at high pH. Moreover, the gelling action of the thickening agent should preferably occur at any pH and should not require an increased pH as is required by acrylic acid based gelling agents of the prior art. In fact acrylic based gelling agents are considered unstable because they need high pH to gel thus destabilizing the hydrogen peroxide, and are as such less desirable. The gelling action should also be thermo-reversible, i.e., the gel should liquefy at low temperature and the liquefied solution should be able to revert back to a gel once warmed up to room temperature.

The bleaching gel described herein has a viscosity range as follows: 4° C.—less than 200 CP's; 20° C.—approximately 2000 CP's and 24° C.—approximately 5000 CP's.

The preferred thickening agent having all of the above properties is Pluronic, a copolymer of polyethylene oxide and polypropylene oxide. Most preferred is a hydrophilic variety of Pluronic namely Pluronic F127 (also known as Poloxamer 407) a trade name of BASF, which gels at room temperature (at about 20° C.) in water. This gelling agent is very stable and not prone to oxidation by $H_2O_2$ probably due to absence of unsaturation and/or active sites in the molecule. Pluronic also acts as a surfactant, which helps to remove extrinsic stains from teeth. In addition to Pluronic, a small amount of glycerol and sodium chloride (at 5% concentration) may be used to impart optimal viscosity to the formulation. It is to be noted that more gelling agent (Pluronic F 127) would be required to gel a hydrogen peroxide solution than would be required to gel a pure water based solution, due to the gel-weakening effects imparted by the additives in the hydrogen peroxide solution.

In view of the acidity of the stabilized $H_2O_2$ solution, the formulation pH may have to be raised slightly so that the gel would not etch the enamel of the teeth. However the pH should be kept below 7 and in a range of from about 3 to about 7, and most preferably from about 4 to about 6. The preferred neutralizing agent includes alkali hydroxides such as sodium and potassium hydroxides, amines such as disisopropanol and triethanolamines, ammonium hydroxide and the like. The most preferred neutralizing agent is 50% sodium hydroxide, 50% solution in deionized water. A carrier may also be added to adjust the bleaching agent concentration and for good dispersion of the dye and peroxide and also for achieving optimal viscosity of the formulation. The carrier used may be water alone or in combination with another viscosity enhancing agent known to those skilled in the art such as glycerol, sorbitol, polypropylene glycol, polyethylene glycol, propylene glycol, sterol alcohol, large molecular weight, polygols, or mixtures of the foregoing, and equivalents.

Bleaching Agent Stabilizers

The stabilizers used act as scavengers of errant metal ions, which can potentially destabilize the $H_2O_2$. Stabilizing action is also prevented by antioxidants which themselves get oxidized in preference to other components of the formulation. Additionally, the peralkali grade of $H_2O_2$ contains stabilizers typical for $H_2O_2$ such as tin phosphates/phosphonates, phosphoric acid, and tin sulphonates. Also amino phosponates chelants may be used as stabilizers. The three (3) classes of stabilizers used in this formulation include antioxidants such as sodium sulfite, metal chelants such as EDTA di sodium and stabilizers meant specifically for $H_2O_2$ such as tin salts, phosphoric acid, etc.

Dye

Any FD & C approved dye may be used in the bleaching composition of the present invention although aesthetically attractive water soluble FD & C approved dyes are preferred such as FD & C Red 40 or FD & C Yellow 5 or FD & C Yellow 6. FD & C approved dyes cannot be used in other bleaching formulas because the $H_2O_2$ would cause them to breakdown under normal shelf life conditions (i.e. 6 months to one year). The use of a dye prevents an accidental application of the bleaching composition to the gingiva since it can be easily seen and provides the user with a control mechanism to time the duration of the bleaching operation and bleaching action. The red and yellow dyes can be used to create orange or yellow bleach formulas which can be specifically "tuned" to absorb energy on the 360–500 nanometer range which is where dental curing lights typically operate. In addition, the red dye can be used to create a bleach formula, which will absorb infrared energy from dental curing light, which also increases the release of hydroxyl and perhydroxyl free radicals. This feature of heating up the bleaching agent further enhances acceleration and release of hydroxyl and perhydroxyl free radicals. Moreover, a dental curing light may also be utilized for this purpose.

Activator System

Our dental bleaching gel can be activated to unleash the bleaching action of hydrogen peroxide by three (3) types of agents. Each activating agent destabilizes hydrogen peroxide in its own unique way, a brief description of which is provided below:

1. Metal ions: Ions of metals belonging to transition group in the periodic table i.e. metals such as iron, cobalt, nickel, copper, zinc, manganese, chromium, etc. are known to catalyze decomposition of hydrogen peroxide in solution, thus unleashing the bleaching action. Of these, in our case, the chloride salt of manganese seemed to be the most effective in activating the gel. In our work, iron salts (sulfate) were also tried but did not prove as effective, probably due to the lowering of pH of the solution by the iron salt, which in turns tries to stabilize hydrogen peroxide. Managanese salts, on the other hand, when dissolved in water, does not affect the pH of the solution and leads to a controlled destabilization of hydrogen peroxide. In this context, it should be mentioned that literature cites other manganese sales such as citrate and gluconate as activators. However, in view of the fact that Manganous Chloride (Sulfate is slightly less than Chloride in solubility) is much more soluble than the citrate or gluconate salt in water, it is no surprise that Manganous Chloride proved to be the most effective in activating the gel.

2. High pH: Hydrogen peroxide is known to get destabilized and release hydroxyl and perhydroxyl free radicals and oxygen gas in high pH (>7) environment. Thus, our gel can be activated by raising the pH of the gel by adding Sodium carbonate or Bicarbonate (Addition of Sodium Hydroxide would lead to very high pH which would be toxic and hence is not recommended) to it. In the earliest stages of this project, baking soda (Sod. Bicarb.) was indeed used to activate the gel. Later, however, the activation with Manganese Chloride solution proved to be more expedient and more reproducible.

3. Enzyme: Catalase, an Organo-metallic enzyme containing iron, can specifically activate a very large amount of hydrogen peroxide, mole per mole. Using this enzyme, a very large amount of hydroxyl free radicals and hence a large amount of oxygen, would be released in a very short time which would in turn may provide good bleaching action. However, the very active evolution of oxygen may lead to gel carry over into gingiva, leading to irritation. Also, it has been reported in literature that the destabilizing action provided by catalase may not necessarily provide a concomitant extensive bleaching action due to a different mechanism of destabilization.

The bleaching gel 6 of the present invention is adapted to be activated by an activator system. The activator system includes an applicator 4 with a brush 7 at one end containing impregnated activating material 8 which accelerates the bleaching action of the peroxide bleaching agent substantially simultaneous with the application of the bleaching gel to a tooth or teeth to be bleached. The applicator 4 as shown in FIGS. 1(*a*) and 1(*b*) is represented by a stem or handle extending from the brush 7 and an activator 8. The handle or stem of the applicator 4 may be formed of any desired material such as plastic and may be straight or bent. The brush 7 should be a microbrush of miniature size composed of multiple tufted fibers having interstices adapted to retain the dried particles of activating material 8. The fibers of the small tufted brush 7 may be synthetic such as nylon or may be of natural fibers and may be in the form of a mesh or other woven or unwoven configuration provided multiple interstices are formed to store the dried particles of activating material 8. The applicator 4 and brush 7 is similar to many commercially available miniature brushes designed for dental use.

The activating material 8 consists of dried particles of a compound selected from the group consisting of a catalyst, an enzyme or a pH modifier adapted to increase the pH of the bleaching composition to above at least 8 and preferably above 10 upon direct contact with the bleaching gel 6. A preferred activator material 8 is a compound selected from the group consisting of Manganous Chloride, Manganous Citrate, Ferrous Sulfate, Sodium Carbonate, Sodium Bicarbonate and Catalase.

Cotton rolls 1 and an isolation material commonly called "rubber dam replacement" 2, is used to keep the peroxide gel from impinging on the gingiva.

The micro brush 7 is dipped into an aqueous solution of the preferred activator material 8 and dried to retain the activator material 8 impregnated therein. The brush 7 impregnated with dried particles of the activating material 8 is used to spread the dispensed gel 6 upon the surfaces 3 of the teeth 2 which causes the gel 6 to be uniformly activated at the same time. The dried particles of activating material 8 in the micro brush 7 are transferred by physical and capillary action to the bleaching gel 6. The applicator 4 can be manipulated by any person for use to readily pick up the bleaching gel 6 from the pad 5 and to apply the bleaching gel 6 to a tooth surface 3 as shown in FIG. 1(*a*). The dried particles of activating material 8 cause immediate acceleration of the peroxide bleaching agent in the gel 6 upon contact with the gel 6 on the brush 7.

The preferred activator system 8 of the present invention consists of a small tufted brush 7 soaked in a chemical activator solution in a range of from about 10–40%, more preferably 15–30%, most preferably 20% solution of activator such as manganous chloride ($MnCl_2$) in water, and dried before use. The dried brush impregnated with the dried particles of activator is used to apply the bleaching gel onto the teeth and in the process activate the $H_2O_2$, releasing a large amount of free hydroxyl and perhydroxyl radicals and oxygen bubbles within one (1) to two (2) minutes of contact. Manganous chloride ($MnCl_2$) in water is the preferred activator although the following other activating agents may be used:

Catalase solution—0.005 to 0.01% concentration (w/v) in water

15–20% Sodium Carbonate or bicarbonate solution in water

15–20% Ferrous Sulfate solution in water

5–10% Manganous Citrate solution in water

An alternate embodiment of this invention would be a formulation of activator, which incorporates an FD & C or other dye system into the activator. In this embodiment, a dye that changes color during the whitening process.

The following tables teach the desired ranges for the constituents of the bleaching gel 10, provide examples various bleach formulations, activation results and a summary of the effects of the use of activators.

TABLE 1

Compositional ranges of various constituents used in the dental bleaching gel

| INGREDIENT | RANGE |
|---|---|
| (a) Pluronic F 127 | 50–70 (w/v) |
| (b) Glycerol | 5–15 (v/v) |
| (c) Sodium Sulfite | 0.2–1 (w/v) |
| (d) Edetate disodium | 0.1–.05 (w/v) |
| (e) FD & C Red 40 or FD & C Yellow 5 or FD & C Yellow 6 | 0.015–0.04 (w/v) |
| (f) Sodium Chloride | 5–7% (w/v) |

TABLE 2

Amounts of various constituents used in four (4) example batches of dental bleaching gel per 100 m. of 35% Degussa Peralkali Hydrogen Peroxide solution

| Ingredients | Example 1 | Example 2 | Example 3 | Example 4 |
|---|---|---|---|---|
| (a) | 64 gm | 64 gm | 80 gm | 60 gm |
| (b) | 0 | 2 ml | 4 ml | 5 ml |
| (c) | 0.3 g | 0.3 | 0.2 | 0.2 |
| (d) | 0.2 | 0.2 | 0.1 | 0.1 |
| (e) | 0.02 | 0.03 | 0.02 | 0.02 |
| (f) | 5 | 5 | 7 | 5 |

Observations Corresponding to Examples in Table 2

EXAMPLE 1

The viscosity of the gel was too low; the gel flowed easily down a horizontal surface. This formulation was rejected.

EXAMPLE 2

The viscosity of this gel was deemed optimum. It was not too low that it did not run down a horizontal surface and that it was not too high that prevented it from dispensing from a syringe. No bubbles were formed in the gel on standing and its viscosity was sustained when stored in the refrigerator. Additionally, the color of the gel remained stable until the gel was activated with an activator solution.

EXAMPLE 3

The viscosity of this gel was too high to be dispensed from a syringe. Also, the gel had a lumpy consistency, which would be aesthetically unacceptable.

EXAMPLE 4

The viscosity of this gel was optimum and the gel behaved very similarly to the gel described in Example #2. This formulation would be acceptable.

Table 3, as follows, shows the strength and pH of various activating agents.

TABLE 3

Activation studies used for activating dental bleaching gel

| Sample # | Type | Strength % (w/v) | PH |
|---|---|---|---|
| 1 | $MnCl_2$ | 10 | 7.0 |
| 2 | $FeSO_4$ | 10 | 3–4 |
| 3 | $Na_2CO_3$ | 10 | 10–11 |
| 4 | Catalase | 0.0075 | 7.0 |

TABLE 4

Summary of effects of various activating agents on OXYGEN RELEASE AND DYE DECOMPOSITION

| Sample # | After 3 mins | After 6 mins | After 10 mins | After 15 mins | After 30 mins | After 50 mins |
|---|---|---|---|---|---|---|
| 1 | No bubbles | Profuse bubbling | Continued bubbling | Continued bubbling | Dye color fading, viscosity decreased | Due color fading, bubbling continuing |
| 2 | No bubbles | Minimal bubbling | Minimal bubbling | Minimal Bubbling | Profuse bubbling, due color fading, viscosity decreased | Continued bubbling, red color fading |
| 3 | No bubbling | Minimal bubbling | Minimal bubbling | Minimal Bubbling | Minimal bubbling | Discernable bubbling |
| 4 | Instantaneous bubbling | Profuse bubbling | Profuse bubbling | Profuse Bubbling | Considerable bubbling | Dye color fading, bubbling continuing |

What we claim is:

1. A dental bleaching composition for bleaching and whitening the teeth of a mammal comprising a peroxide bleaching agent, a thickening agent for forming a viscous gel, an FD & C approved dye and at least one bleaching agent stabilizer for minimizing the affect of said peroxide bleaching agent on dye discoloration during storage of the peroxide bleaching agent and dye for use in combination with an enzymatic activator comprising Catalase to cause sufficient catalytic activation of said peroxide bleaching agent for whitening said teeth.

2. A dental bleaching composition as defined in claim 1 wherein said bleaching composition has a pH of less than 7.

3. A dental bleaching composition as defined in claim 1 wherein said FD & C approved dye is selected from the group consisting of FD & C Red dye and a FD & C Yellow dye.

4. A dental bleaching composition as defined in claim 1 wherein said bleaching agent stabilizer further includes a metal ion scavenger and/or an antioxidant.

5. A dental bleaching composition as defined in claim 3 wherein said bleaching agent stabilizer is selected from one or more of the group consisting of tin phosphates, tin phosphonates, amino phosphonates, sodium sulfite and a metal chelate such as EDTA di sodium.

6. A dental bleaching composition as defined in claim 4 wherein said thickening agent comprises a copolymer of polyethylene oxide and polypropylene oxide.

7. A dental bleaching composition as defined in claim 6 wherein said thickening agent further comprises glycerol and a chloride salt.

8. An activator system for activating a peroxide bleaching composition containing a peroxide bleaching agent to bleach and whiten teeth, said activator system including dried particles of a soluble activator comprising Catalase for accelerating the bleaching action of said peroxide bleaching agent and an applicator for storing the dried particles of activator separated from the bleaching composition such that upon contacting the applicator to the bleaching composition the peroxide bleaching agent is activated by substantially simultaneous application of the applicator to the teeth to be bleached.

9. An activator system as defined in claim 7 wherein said bleaching composition further comprises a bleaching agent stabilizer and has a pH of below 7.

10. An activator system as defined in claim 8 wherein said applicator comprises a stem having a tip at one end covered with synthetic or natural fibers integrated to form bristles having interstices adapted to retain said dried particles of activator.

11. An activator system as defined in claim 9 wherein said applicator further comprises a dye.

12. An activator system as defined in claim 10 wherein said activator further comprises a catalyst selected from the group consisting of Manganous Chloride, Manganous Citrate and Ferrous Sulfate.

13. A method for applying and activating a dental bleaching gel upon a tooth surface for cosmetically whitening the tooth and/or for the treatment of stains or discolorations comprising the steps of;
   formulating a stabilized dental bleaching composition comprising a peroxide bleaching agent, a thickening agent to form a viscous gel, and at least one stabilizer for said peroxide bleaching agent with the bleaching composition having a pH of less than 7;
   forming an activator system to accelerate the bleaching action of the bleaching composition with the activator system comprised of a soluble activator of dried particles of Catalase and an applicator in which the dried particles of Catalase are stored for applying the activator and bleaching composition simultaneously to the tooth or teeth to be bleached;

contacting the applicator containing the stored dried particles of activator to the stabilized dental bleaching composition; and applying the applicator following contact with the bleaching composition to the tooth or teeth surfaces to be bleached such that the bleaching gel composition is uniformly activated on the tooth or teeth to be bleached simultaneously upon contact with the tooth or teeth to be bleached.

14. A method as defined in claim 12 with said stabilized dental bleaching composition including at least one FD & C approved dye.

15. A method as defined in claim 13 wherein said applicator comprises a, stem having a tip at one end covered with synthetic or natural fibers integrated to form bristles having interstices adapted to retain said dried particles of activator.

16. A method as defined in claim 14 wherein said dried particles of activator are stored in said applicator by dipping the applicator in an aqueous solution of said activator and drying said applicator.

17. A method as defined in claim 15 wherein said thickening agent is comprised of a hydrophilic copolymer of polyethylene oxide and polypropylene oxide.

18. A method as defined in claim 16 wherein said thickening agent further comprises glycerol and a chloride salt.

* * * * *